United States Patent
Yanuma et al.

(10) Patent No.: US 8,795,273 B2
(45) Date of Patent: Aug. 5, 2014

(54) TREATMENT TOOL FOR ENDOSCOPE

(75) Inventors: Yutaka Yanuma, Tokyo (JP); Hideki Fujii, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 280 days.

(21) Appl. No.: 13/179,692

(22) Filed: Jul. 11, 2011

(65) Prior Publication Data

US 2012/0016190 A1 Jan. 19, 2012

Related U.S. Application Data

(63) Continuation of application No. PCT/JP2010/070119, filed on Nov. 11, 2010.

(30) Foreign Application Priority Data

Jan. 18, 2010 (JP) ................. P2010-008002

(51) Int. Cl.
- *A61B 18/18* (2006.01)
- *A61B 18/16* (2006.01)
- *A61B 17/32* (2006.01)
- *A61B 18/14* (2006.01)
- *A61B 17/221* (2006.01)
- *A61B 18/00* (2006.01)

(52) U.S. Cl.
CPC ........... *A61B 18/1492* (2013.01); *A61B 18/16* (2013.01); *A61B 2017/320064* (2013.01); *A61B 2018/141* (2013.01); *A61B 2017/2215* (2013.01); *A61B 2018/1407* (2013.01); *A61B 2018/00595* (2013.01); *A61B 2018/00601* (2013.01)
USPC ................. 606/47; 606/45; 606/46

(58) Field of Classification Search
CPC ............... A61B 2018/1475; A61B 2018/1407; A61B 2018/141; A61B 2018/144; A61B 2018/1405; A61B 2018/00607; A61B 2018/00601
USPC ....................... 606/110–115, 45–47
See application file for complete search history.

(56) References Cited

U.S. PATENT DOCUMENTS

| | | | |
|---|---|---|---|
| 4,311,143 A | 1/1982 | Komiya | |
| 6,254,600 B1 | 7/2001 | Willink et al. | |
| 6,905,495 B1 * | 6/2005 | Fuimaono et al. | 606/41 |

FOREIGN PATENT DOCUMENTS

| | | |
|---|---|---|
| JP | S61-9051 | 3/1986 |
| JP | 11-47149 | 2/1999 |
| JP | 2002-224135 | 8/2002 |
| JP | 2004-057454 | 2/2004 |
| JP | 2007-54584 | 3/2007 |
| WO | WO 98/03117 A1 | 1/1998 |

OTHER PUBLICATIONS

International Search Report dated Dec. 21, 2010 together with English translation.
European Search Report dated May 25, 2012 from corresponding European Patent Application No. EP 10 843108.1.

* cited by examiner

*Primary Examiner* — Jaymi Della
(74) *Attorney, Agent, or Firm* — Scully, Scott, Murphy & Presser, P.C.

(57) ABSTRACT

In this treatment tool for endoscope, a sheath includes, at the distal end thereof, a tubular extended part having a predetermined thickness in the radially outward direction from an inner peripheral face of a first hole and extending further to the distal-end side, and a passive electrode is disposed such as to surround the outer periphery of the extended part.

7 Claims, 13 Drawing Sheets

TREATMENT TOOL FOR ENDOSCOPE

BACKGROUND OF THE INVENTION

1. Field of the Invention

The present invention relates to a treatment tool for endoscope used with an endoscope.

This application is a continuation application based on PCT Patent Application No. PCT/JP2010/070119, filed on Nov. 11, 2010, which claims priority to Japanese Patent Application No. 2010-008002, filed on Jan. 18, 2010. The contents of PCT Patent Application No. PCT/JP2010/070019 and Japanese Patent Application No. 2010-008002 are incorporated herein by reference.

2. Description of Related Art

There is a conventionally known treatment tool for endoscope that is inserted into an endoscope and carries out treatment to a living tissue and the like. Some such treatment tools for endoscope include a mechanism that conducts a high-frequency current to the treatment tool to carry out treatment to the living tissue such as, for example, cutting, cauterization, and arrest of bleeding.

As an example of such a treatment tool for endoscope, Japanese Examined Patent Application, Second Publication No. S61-9051, discloses a high-frequency cutting tool for cutting a living tissue with a snare which a high-frequency electric current is passed through. The high-frequency cutting tool described in this patent document includes a sheath including electrically insulating outer and inner pipes, an operation wire that is inserted in the sheath and can be operated on the hand side of the sheath such that it can advance and retreat, a snare connected to the distal end of the operation wire, an electrode that is exposed and fixed at a distal-end part of the sheath and contacts the living tissue, and means of inserting the electrode and the snare into the sheath and making each of them conductive with a high-frequency generator.

According to this high-frequency cutting tool, the living tissue that is the cutting object is gripped by the snare, and a high-frequency current is conducted to the snare, whereby the living tissue can be cauterized.

Furthermore, Japanese Patent Application, First Publication No. 2004-57454, discloses a bipolar high-frequency treatment tool for endoscope. The bipolar high-frequency treatment tool for endoscope includes a multi-lumen tube with a pair of guide holes formed therein, and conductive operation wires inserted into each of the pair of guide holes.

According to this bipolar high-frequency treatment tool for endoscope, sufficient electrical insulation can be ensured between the pair of conductive operation wires inserted into the multi-lumen tube.

SUMMARY OF THE INVENTION

According to the invention, a treatment tool for endoscope includes an elongated insulating sheath including a first hole and a second hole which extend in the axial direction of the sheath and are open at both ends of the sheath, an electrically conductive wire that is inserted into the first hole so as to be able to advance and retreat, and includes a high-frequency treatment part at a distal end of the wire, an operation part for making the wire advance and retreat with respect to the sheath, the operation part being connected to a proximal end of the wire, a passive electrode that is insulated from the wire and fixed to the distal end of the sheath, the passive electrode including a hole being coaxial to the second hole and communicating to the second hole, an electric cable that is inserted into the hole formed in the passive electrode and electrically connected to the passive electrode, the electric cable being mechanically fixed to the passive electrode and inserted into the second hole, and a pair of supply electrodes that are electrically connected to each of the electric cable and the wire, and supply a high-frequency current to them. The sheath includes, at the distal end thereof, a tubular extended part having a predetermined thickness in the radially outward direction from an inner peripheral face of the first hole and extending further to the distal-end side. The passive electrode is disposed such as to surround the outer periphery of the extended part.

The sheath may be a multi-lumen tube in which a through-hole having a circular cross-section formed as the first hole, and a through-hole having a circular cross-section formed as the second hole, are disposed to be spaced apart from each other in the radial direction of the sheath.

The outer-diameter dimensions of the passive electrode measured in the radial direction of the sheath may be smaller than the outer-diameter dimensions of the sheath.

The central axis of the extended part may be eccentric to the central axis of the sheath.

An outer peripheral face of the extended part, and a face that is facing the outer peripheral face of the extended part among the outer faces of the passive electrode, may be positioned using a protrusion/recess structure wherein they fit together.

The protrusion/recess structure may have a linear shape extending in the circumferential direction of the extended part.

The protrusion/recess structure may be a linear shape extending parallel to the central axis of the extended part.

The outer diameter of the extended part may be smaller than the maximum outer diameter of the sheath.

The high-frequency treatment part may be a high-frequency snare having a flexible snare loop shaped like a closed ring.

The high-frequency treatment part may be a high-frequency cutting treatment tool having a needle extending in the axial direction of the wire.

The high-frequency treatment part may be a two-legged high-frequency treatment tool having a pair of gripping parts that may open and close, and capable of cutting a living tissue.

DETAILED DESCRIPTION OF THE INVENTION

A treatment tool for endoscope in an embodiment of the invention will be explained with reference to FIG. 1 and FIG. 2.

Figure 1:
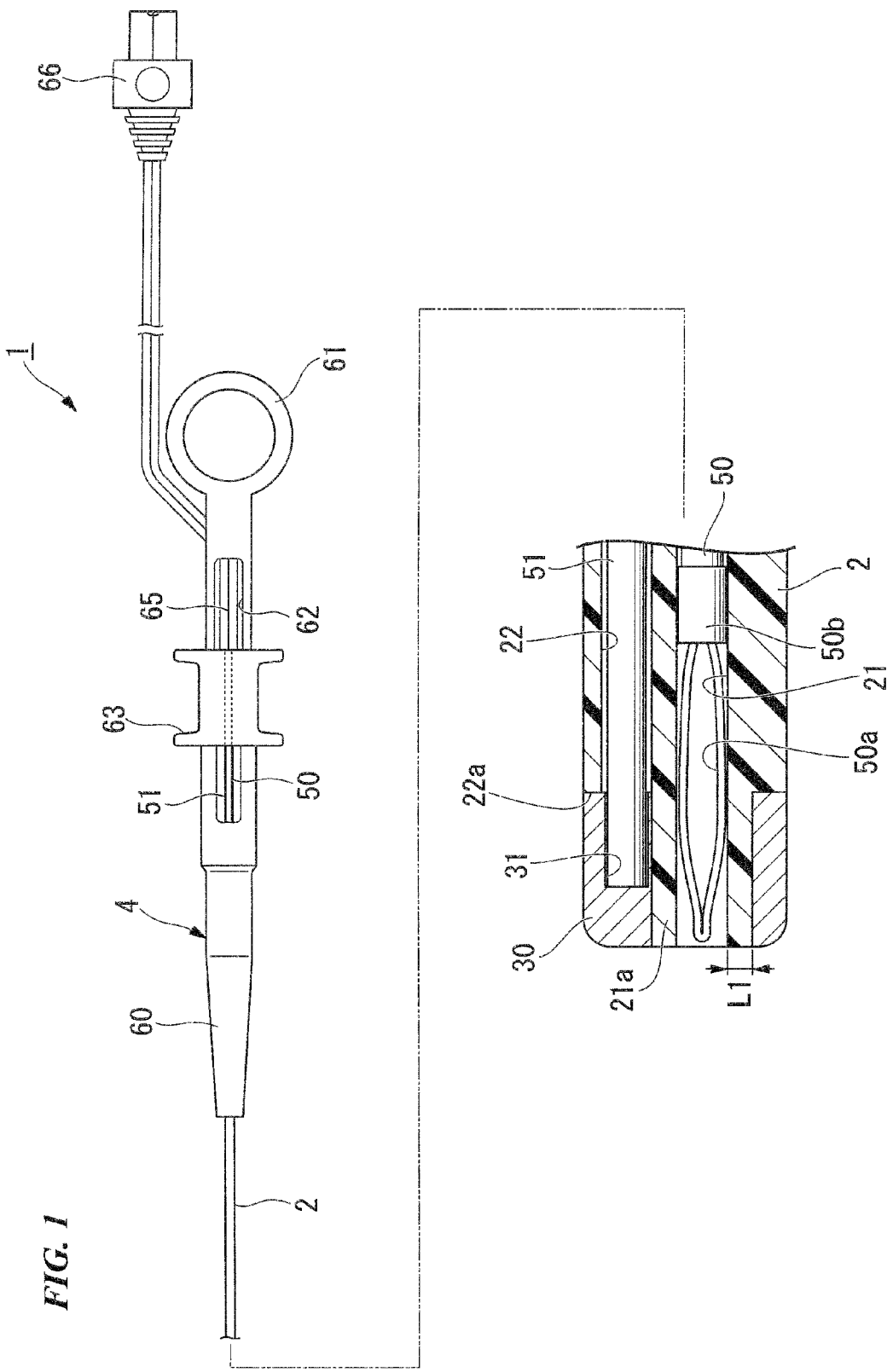
FIG. 1 is a side diagram of a treatment tool for endoscope in an embodiment of the invention, showing a partial cross-section thereof.

FIG. 1 is a side diagram of a treatment tool for endoscope 1, showing a partial cross-section thereof. The treatment tool for endoscope 1 includes an elongated sheath 2 that is inserted into a body cavity, and an operation part 4 that is connected to a proximal-end side of the sheath 2 and is used by a user who operates the treatment tool for endoscope 1.

In the sheath 2, a first hole 21 and a second hole 22 are formed, which extend in the axial direction of the sheath 2 and are open at both ends of the sheath 2. The sheath 2 is made from an insulating material such as, for example, an insulating resin. The sheath 2 is preferably flexible enough to be able to advance and retreat along the curve of a hollow tissue or the like inside a living body.

At the tip of the sheath 2, an extended part 21a is formed such that the distal end of the first hole 21 opens at a position extended further to the distal-end side than a distal-end face 22a of the second hole 22. The extended part 21a is formed in a shape achieved by shaving the outer peripheral face of the distal-end side of the sheath 2, and is formed in a tube-like shape having a predetermined thickness L1, the outer diameter of the extended part 21a being smaller than the outer diameter of an intermediate part of the sheath 2. In the present invention, the 'tube-like shape' of the extended part 21a is not limited to a cylindrical shape where the contour of the outer shape of the extended part 21a in radial cross-section is a circle. That is, the extended part 21a need only be shaped such that the first hole 21 is formed to the distal-end side from the proximal-end side and opens to the outside on the distal-end side, there being no other limitations on its shape. Moreover, the shape of the contour of the open end part of the first hole 21 at the distal end of the extended part 21a is also not limited to a circle. The shape of the extended part 21a will be explained in more detail later.

A passive electrode 30 having electrical conductivity is fixed to the outer peripheral face of the extended part 21a. The passive electrode 30 is disposed at a distance equal to the predetermined thickness L1 of the extended part 21a from an inner wall face of the extended part 21a. The outer diameter of the passive electrode 30 is preferably no larger than the outer diameter of the sheath 2. A hole 31 is formed in the passive electrode 30 and is coaxial with the second hole 22. Preferably, the distal end of the passive electrode 30 is disposed at the same position as the distal end of the extended part 21a, or further to the proximal-end side than the distal end of the extended part 21a.

An electrically conductive wire 50 has, at its distal end, a snare loop 50a constituting a high-frequency treatment part, and is inserted into the first hole 21 so as to be able to advance and retreat. In this embodiment, the wire 50 and the snare loop 50a are inserted into a connection pipe 50b together and fixed by brazing. The connection between the wire 50 and the snare loop 50a is not limited to brazing, and can be accomplished by welding or crimping. It is also possible to configure the snare loop 50a and the wire 50 in a single structure without the connection pipe 50b. The proximal end of the wire 50 extends from the sheath 2 to the operation part 4 side.

An electroconductive electric cable 51 is inserted into the second hole 22, the tip of this electric cable 51 being inserted into a hole 31 in the passive electrode 30 and electrically connected thereto. The electric cable 51 extends through the second hole 22 to the operation part 4 side. The passive electrode 30 and the electric cable 51 are preferably connected by a method such as welding to reduce electrical resistance. Connection can also be accomplished by simply press-fitting the electric cable 51 into the hole 31, or inserting the electric cable 51 into the hole 31 and fixing the electric cable 51 by crimping the passive electrode 30.

The operation part 4 can be configured as a conventionally known operation part of a treatment tool for endoscope. For example, it can include an operation unit 60 including a long hole 62 that is long in the axial direction of the sheath 2 and connects to the sheath 2, a finger-hook ring 61 that is formed at the proximal end of the operation unit 60 and enables a user to grip it with his fingers, and a slider 63 that engages with the outer face of the operation unit 60 and can advance and retreat in the long axial direction of the long hole 62.

The wire 50 and the electric cable 51 extend to the operation part 4. The wire 50 is fixed to the slider 63. Therefore, when the slider 63 is moved in a straight line in the axial direction of the wire 50 with respect to the operation unit 60, the wire 50 is made to advance or retreat with respect to the sheath 2. In this embodiment, when the slider 63 is moved to the furthest point it can move to on the distal-end side of the operation unit 60, the snare loop 50a protrudes from the distal end of the sheath 2, and when the slider 63 is moved to the furthest point it can move to on the proximal-end side of the operation unit 60, the snare loop 50a is completely stored inside the sheath 2.

The operation part 4 is equipped with a power cord 65 having two lead wires, one of which is electrically connected to the wire 50 and the other is connected to the electric cable 51. The power cord 65 includes a connector 66 that can be connected to a high-frequency power supply device (not shown), and thus functions as a supply electrode capable of supplying high-frequency current to the wire 50 and the electric cable 51.

Figure 2:
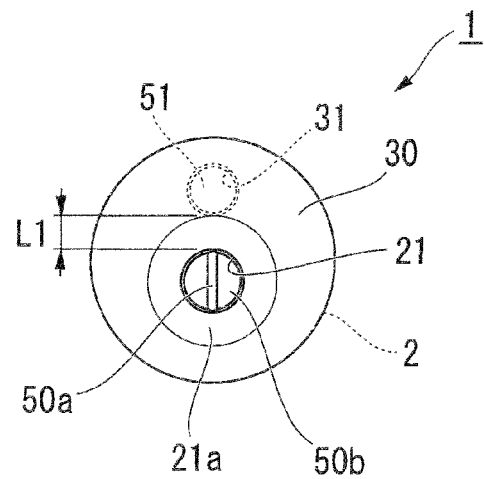
FIG. 2 is a front diagram of the configuration of the distal-end side of the treatment tool for endoscope in the embodiment of the invention.

FIG. 2 is a front diagram of the distal-end side of the sheath 2 of the treatment tool for endoscope 1. Since the passive electrode 30 is shaped such as to have a through-hole that is coaxial to the central axis of the first hole 21, the snare loop 50a is not obstructed from entering and leaving the first hole 21.

Figure 3:
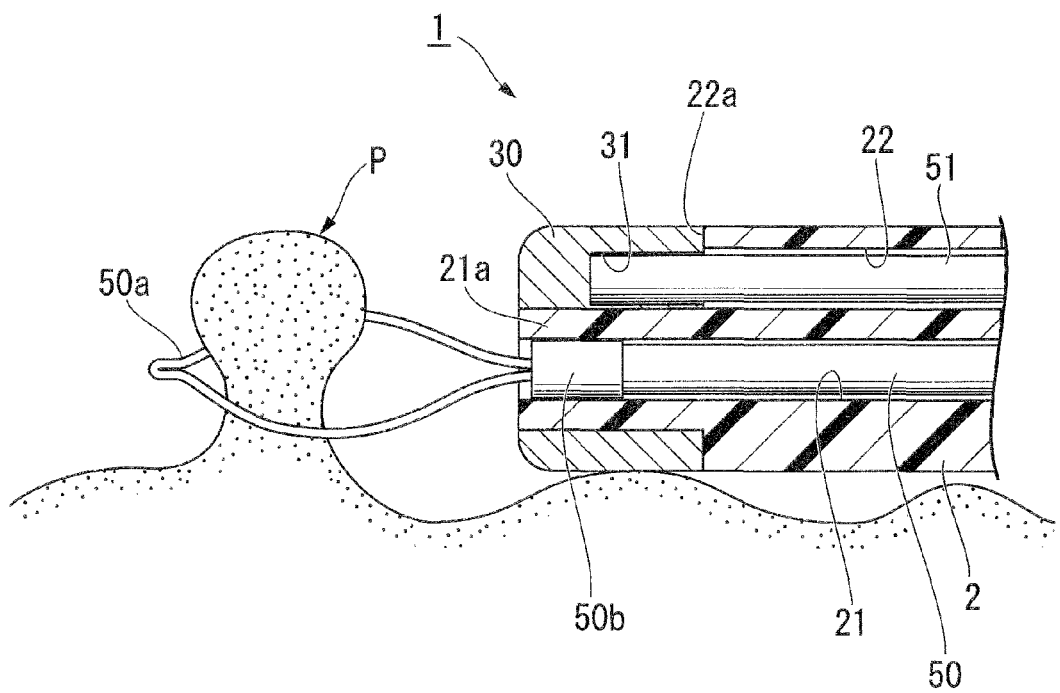
FIG. 3 is a diagram of a process performed when using the treatment tool for endoscope in the embodiment of the invention.
Figure 4:
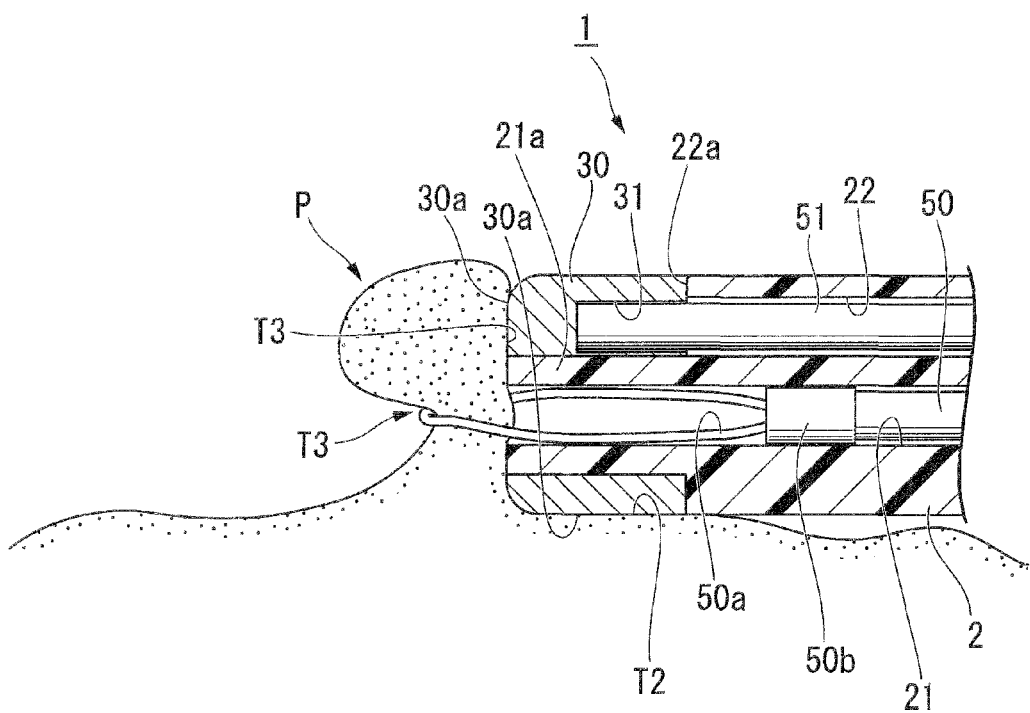
FIG. 4 is a diagram of a process performed when using the treatment tool for endoscope in the embodiment of the invention.

An operation when using the treatment tool for endoscope 1 of this embodiment, configured in the manner described above, will be explained with reference to FIGS. 3 and 4. FIGS. 3 and 4 are diagrams showing a process performed when using the treatment tool for endoscope 1, showing a partial cross-section thereof.

Firstly, a user connects the connector 66 of the power cord 65 of the treatment tool for endoscope 1 to a high-frequency power supply device, enabling high-frequency current to be supplied to the treatment tool for endoscope 1.

Using a well-known technique (not shown), the user inserts an endoscope into a body cavity, guides the distal end of the endoscope to an object portion for treatment, and captures the object portion within the field of view of the endoscope. This embodiment illustrates a process of removing a polyp that has swollen from the top-skin of a living body, as an example of treatment of a living tissue.

As shown in FIG. 3, the user guides the sheath 2 of the treatment tool for endoscope 1 into a body cavity via a route including a forceps channel and the like of the endoscope, and guides the distal end of the sheath 2 to the polyp P that is the treatment object.

The user slides the slider 63 of the operation part 4 shown in FIG. 1 to the distal-end side with respect to the operation unit 60. When he does so, the wire 50 connected to the slider 63 is pressed to the distal-end side with respect to the sheath 2, and the snare loop 50a protrudes from the opening in the extended part 21a forming the distal end of the sheath 2. The snare loop 50a deforms such that it opens in the shape of a ring due to the restoring force generated by its own elasticity. The user loops the snare loop 50a around the polyp P.

The user then slides the slider 63 of the operation part 4 to the proximal-end side of the operation unit 60. When he does so, as shown in FIG. 4, the snare loop 50a is moved in a direction of being stored in the first hole 21 in the sheath 2. At this time, since the snare loop 50a is looped around the polyp P, the polyp P is constricted by the snare loop 50a.

The polyp P constricted by the snare loop 50a is directly contacting the snare loop 50a, and is also being pressed to the distal-end side of the sheath 2. Since the passive electrode 30 is fixed to the distal end of the sheath 2, the polyp P is pressed against an outer face 30a of the passive electrode 30.

The passive electrode 30 may be contacted by parts other than the polyp P. For example, the outer face 30a of the passive electrode 30 may contact a tissue T2 which is a normal, etc.

The user then operates the high-frequency power supply device and supplies a high-frequency current to the treatment tool for endoscope 1. This high-frequency current passes between the electric cable 51 and the snare loop 50a, and generates Joule heat in the tissue T3 between them.

At this time, since the extended part 21a has a predetermined thickness L1, the snare loop 50a constricting the polyp P is prevented from contacting the outer face 30a of the passive electrode 30, and the high-frequency current is appropriately conducted to the tissue T3 between the snare loop 50a and the passive electrode 30.

When the user applies the high-frequency current while constricting the polyp P by the snare loop 50a, the tissue T3 which the high-frequency current is conducted through is cauterized and cut. Therefore, the polyp P is cut off at the section of the tissue T3.

When the polyp P has been cut off, it is delivered outside the body via a suction channel or the like (not shown) of the endoscope. The treatment tool for endoscope 1 and the endoscope are then removed from the body cavity, completing this series of treatments.

As described above, according to the treatment tool for endoscope 1 of this embodiment, since the passive electrode 30 is disposed at the outer periphery of the extended part 21a which protrudes from the distal end of the sheath 2 further to the distal-end side, a simple configuration can achieve sufficient insulation between the passive electrode 30 and the snare loop 50a constituting a high-frequency treatment part.

Also, since the outer diameter of the extended part 21a is smaller than the maximum outer diameter of the sheath 2, the maximum outer diameter of the passive electrode 30 can be prevented from exceeding the maximum outer diameter of the sheath 2 when the passive electrode 30 is fixed in place. This reduces insertion resistance due to the passive electrode 30 sliding against the inner face of a channel, such as a forceps channel of the endoscope, when the sheath 2 is inserted into that channel.

Also, since a multi-lumen tube with the first hole 21 and the second hole 22 formed therein is used as the sheath 2, insulation is favorably maintained between the first hole 21 and the second hole 22. Since the treatment tool for endoscope can be assembled by inserting the wire 50 and the electric cable 51 into the holes, it is convenient to assemble.

Since outer parts of the wire 50 and the electric cable 51 are enclosed by a material with high insulation that constitutes the sheath 2 such that there are no unnecessary gaps, sufficient insulation can be achieved even if the diameter of the sheath 2 is made smaller.

[Modification 1]

A modification of the treatment tool for endoscope of this embodiment will be explained with reference to FIGS. 5 and 6. In the explanation below, parts having like configurations to those of the treatment tool for endoscope described above are designated with like reference codes and are not repetitiously explained.

Figure 5:
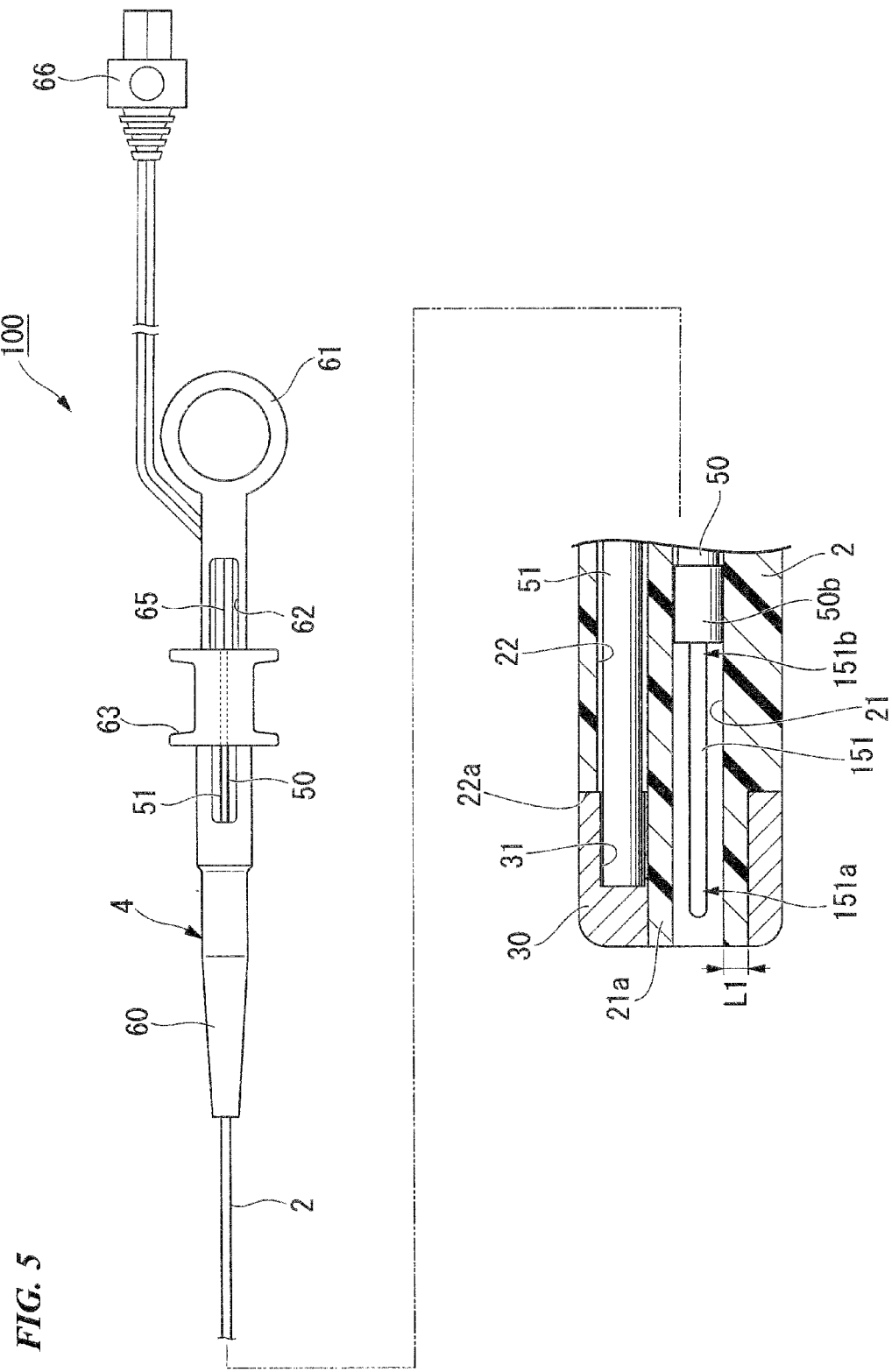
FIG. 5 is a side diagram of a treatment tool for endoscope in modification 1 of the embodiment of the invention, showing a partial cross-section thereof.

FIG. 5 is a side cross-sectional diagram of the configuration of one part of the treatment tool for endoscope according to this modification. As shown in FIG. 5, the configuration of a treatment tool for endoscope 100 of this modification differs from that of the treatment tool for endoscope 1 in that, instead of the snare loop 50a described above, it includes a needle 151 extending in the axial direction of the wire 50. A distal end 151a side of the needle 151 is a section for contacting the living tissue, and a proximal end 151b side is fixed or linked to the wire 50.

The proximal end 151b side of the needle 151 is fixed by a connection pipe 50b which is disposed at the distal end of the wire 50 and covers the outer peripheries of the distal end of the wire 50 and the proximal end of the needle 151. The connection pipe 50b can be configured from, for example, an electrically conductive tubular member containing metal or the like. Provided that the outer shape of the connection pipe 50b is tubular, it can be a cylindrical tube wherein the contour of the radial cross-section is circular, or an angular tube wherein the contour of the radial cross-section is multi-angled. The angles of the outer faces of the connection pipe 50*b* can be formed smoothly to reduce snagging on the inner peripheral faces of the sheath 2.

The connection pipe 50*b* can be configured by arranging the wire 50 and the needle 151 coaxially, or adjacent to each other in the radial direction, and then fixing them by brazing, welding, crimping, etc.

The wire 50 and the needle 151 can be connected directly to each other. Using welding or the like, the distal end of the wire 50 and the proximal end of the needle 151 can be welded together so that they are coaxial or adjacent in the radial direction. Moreover, the needle 151 can be formed in a single piece with the wire 50.

Figure 6:
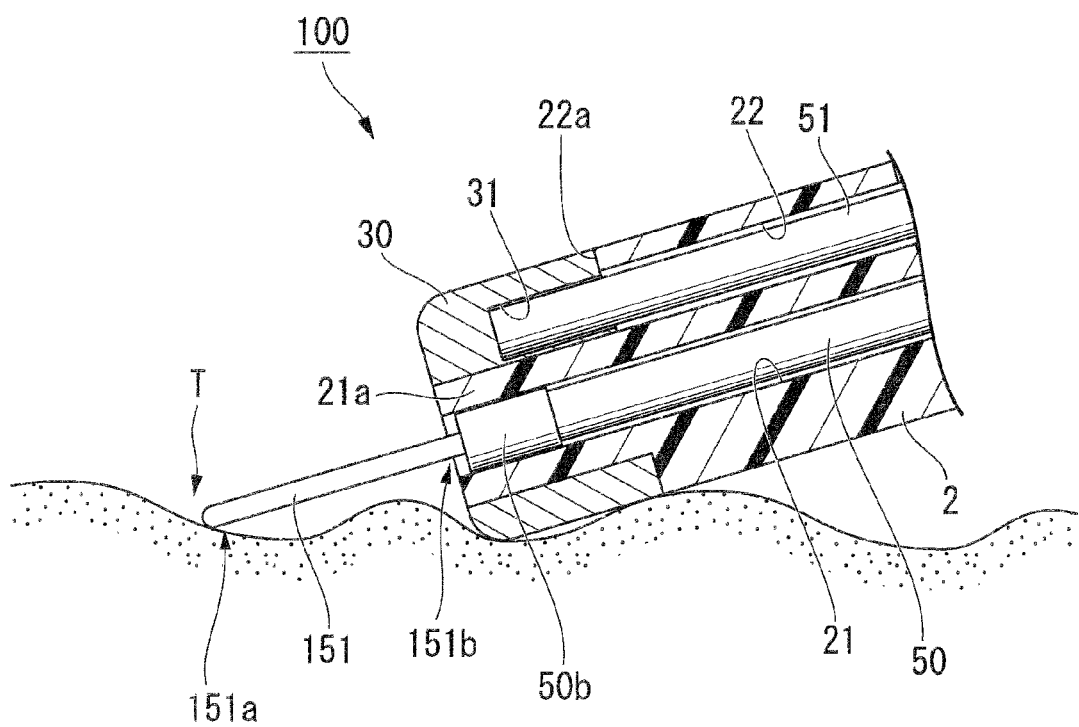
FIG. 6 is a diagram of a process performed when using the treatment tool for endoscope in modification 1.

FIG. 6 is a diagram of a process performed when using the treatment tool for endoscope 100. When using the treatment tool for endoscope 100, due to the advancing and receding of the slider 63 of the operation part 4 (see FIG. 5), the needle 151 protrudes by a predetermined protrusion length from the distal end of the first hole 21 in the sheath 2. The user makes the distal end 151*a* of the needle 151 contact an object portion T that will be the object of treatment, and makes one part of the passive electrode 30 contact the living tissue near this object portion. When the user operates the high-frequency power supply device and supplies a high-frequency current to the treatment tool for endoscope 100, the high-frequency current is conducted to the object portion between the needle 151 and the passive electrode 30. This generates Joule heat in the living tissue between the needle 151 and the passive electrode 30, whereby the object portion is cut off.

In this modification, since the passive electrode 30 is disposed at the outer periphery of the extended part 21*a* which protrudes further to the distal-end side from the distal end of the sheath 2, a simple configuration can achieve sufficient insulation between the needle 151 constituting the high-frequency treatment part and the passive electrode 30.

[Modification 2]

Figure 7:
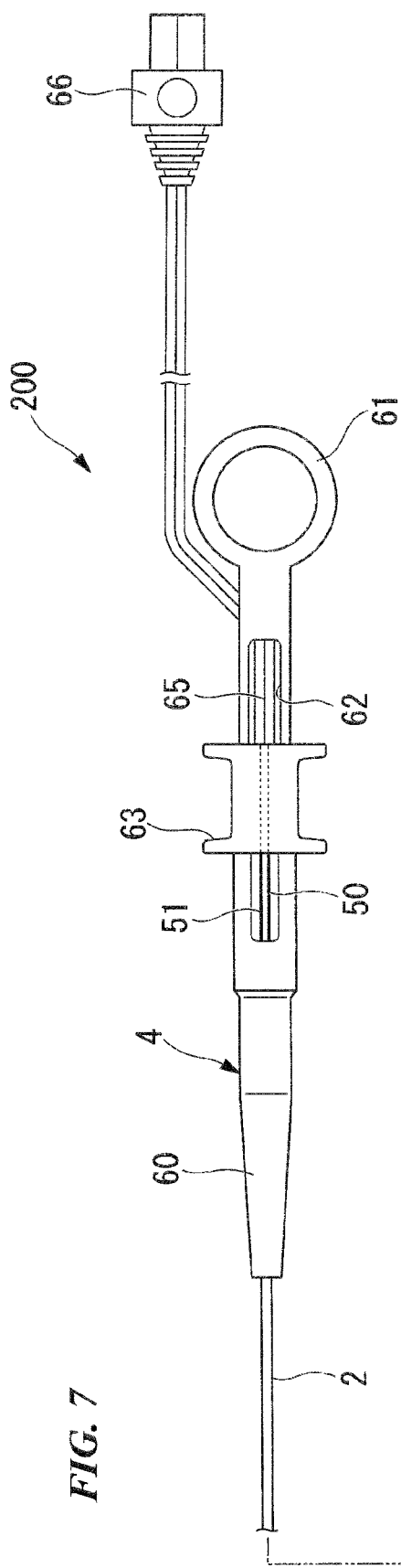
FIG. 7 is a side diagram of a treatment tool for endoscope in modification 2 of the embodiment of the invention, showing a partial cross-section thereof.
Figure 7:
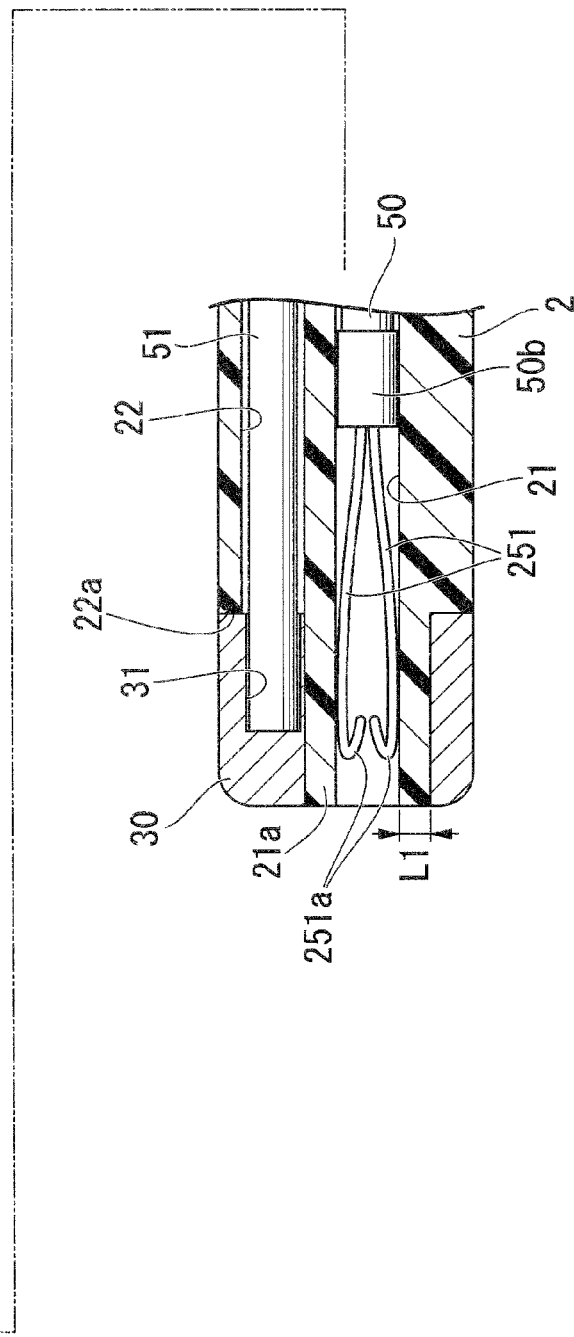

Another modification of the treatment tool for endoscope of this embodiment will be explained with reference to FIGS. 7 to 9. As shown in FIG. 7, the configuration of a treatment tool for endoscope 200 of this modification differs from that of the treatment tool for endoscope 1 described above in that, instead of the snare loop 50*a*, it includes a pair of gripping parts 251 that extend in the axial direction of the wire 50 and can open and close by directly contacting the inner wall of the extended part 21*a*.

The pair of gripping parts 251 includes distal-end parts 251*a* able to contact the object portion that will be the object of treatment. The distal-end parts 251*a* bend towards each other, and, when the pair of gripping parts 251 are manipulated in a closing direction, the distal-end parts 251*a* contact the living tissue that is the object portion. The treatment tool for endoscope 200 of this modification functions as a two-legged high-frequency treatment tool that uses the pair of gripping parts 251 to grip the living tissue.

Figure 8:
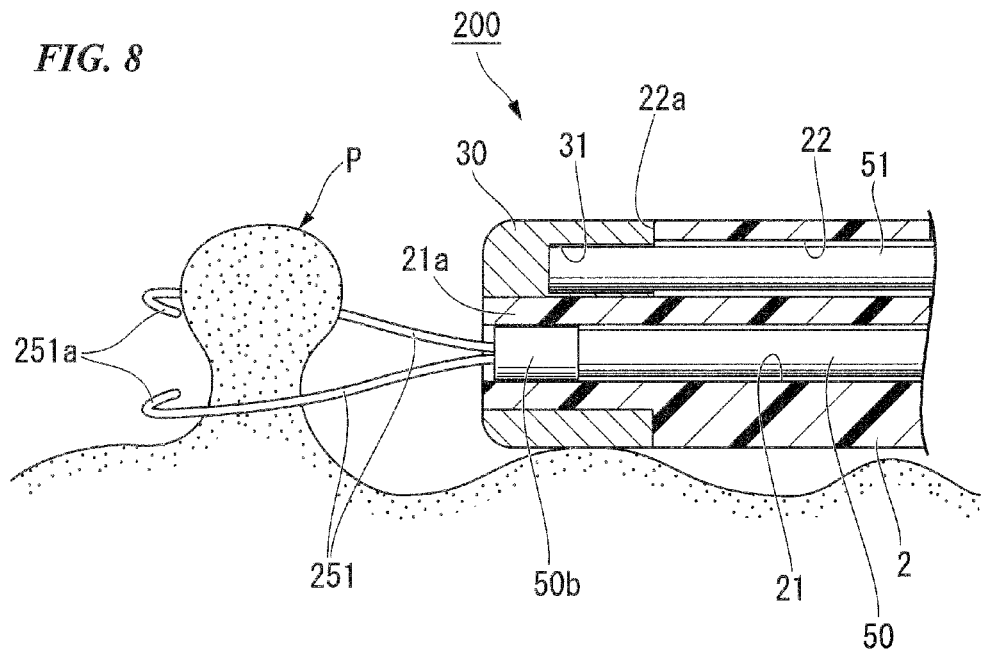
FIG. 8 is a diagram of a process performed when using the treatment tool for endoscope in modification 2.
Figure 9:
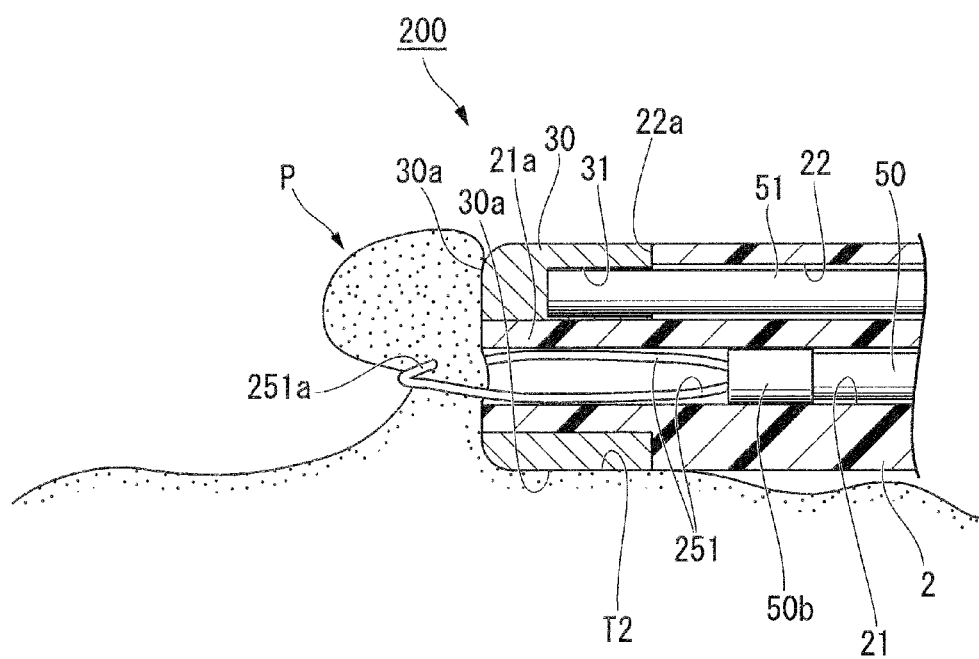
FIG. 9 is a diagram of a process performed when using the treatment tool for endoscope in modification 2.

FIGS. 8 and 9 are diagrams of a process performed when using the treatment tool for endoscope 200. As shown in FIGS. 8 and 9, when using the treatment tool for endoscope 200, due to the advancing and receding of the slider 63 of the operation part 4 (see FIG. 7), the gripping parts 251 protrude by a predetermined protrusion length from the distal end of the extended part 21*a* on the distal-end side of the sheath 2. The user then makes the distal-end parts 251*a* of the gripping parts 251 contact an object portion that is the object of treatment, and makes one part of the passive electrode 30 contact the living tissue near this object portion. When the user operates the high-frequency power supply device and supplies a high-frequency current to the treatment tool for endoscope 200, the high-frequency current is conducted to the object portion between the distal-end parts 251*a* and the passive electrode 30. This generates Joule heat in the living tissue between the distal-end parts 251*a* and the passive electrode 30, whereby the object portion is cut off.

When cauterizing or cutting off the object portion, or when using the gripping parts 251 to grip a living tissue or the like at the object portion, the user advances and retreats the slider 63 of the operation part 4 (see FIG. 7) to move the wire 50 relatively in the axial direction of the sheath 2. This changes the protrusion length of the gripping parts 251 from the distal end of the sheath 2. For example, when the gripping parts 251 move in the direction of being stored inside the sheath 2, contact between the gripping parts 251 and the inner wall of the first hole 21 on the distal-end side of the sheath 2 makes the distal-end parts 251*a* of the gripping parts 251 elastically deform in the closing direction.

In this modification, since the passive electrode 30 is disposed at the outer periphery of the extended part 21*a* which protrudes from the distal end of the sheath 2 further to the distal-end side, a simple configuration can achieve sufficient insulation between the passive electrode 30 and the gripping parts 251 that constitute the high-frequency treatment part.

[Modification 3]

Yet another modification of the treatment tool for endoscope of this embodiment will be explained with reference to FIGS. 10 and 11.

A treatment tool for endoscope 300 of this modification differs from the treatment tool for endoscope 1 described above in regard to the configurations of the passive electrode and the extended part.

Figure 10:
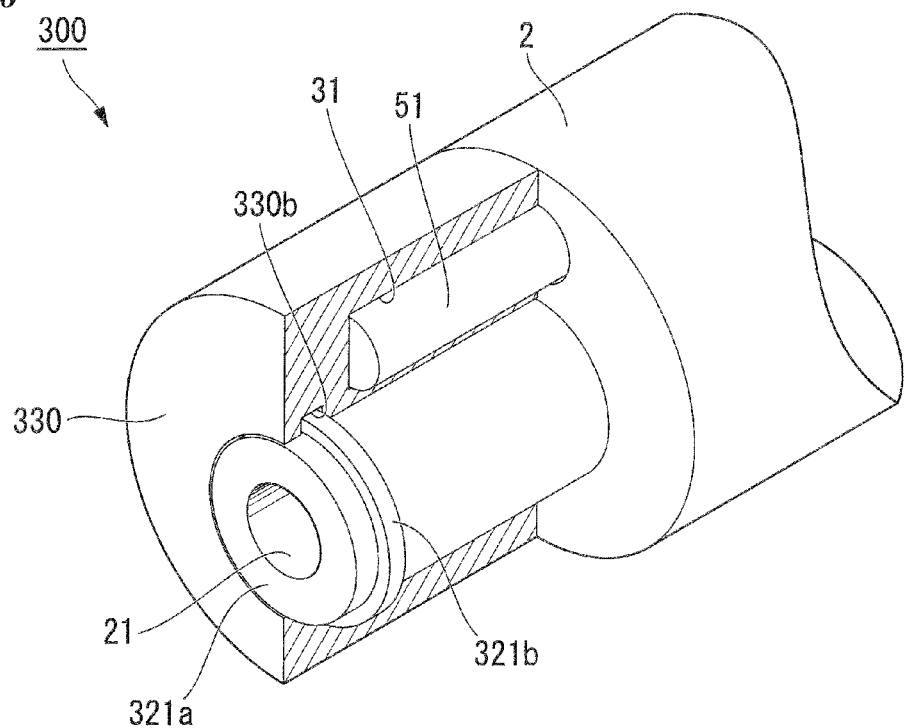
FIG. 10 is a perspective diagram showing an enlargement of one part of a treatment tool for endoscope in modification 3 of the embodiment of the invention, showing a partial cross-section thereof.
Figure 11:
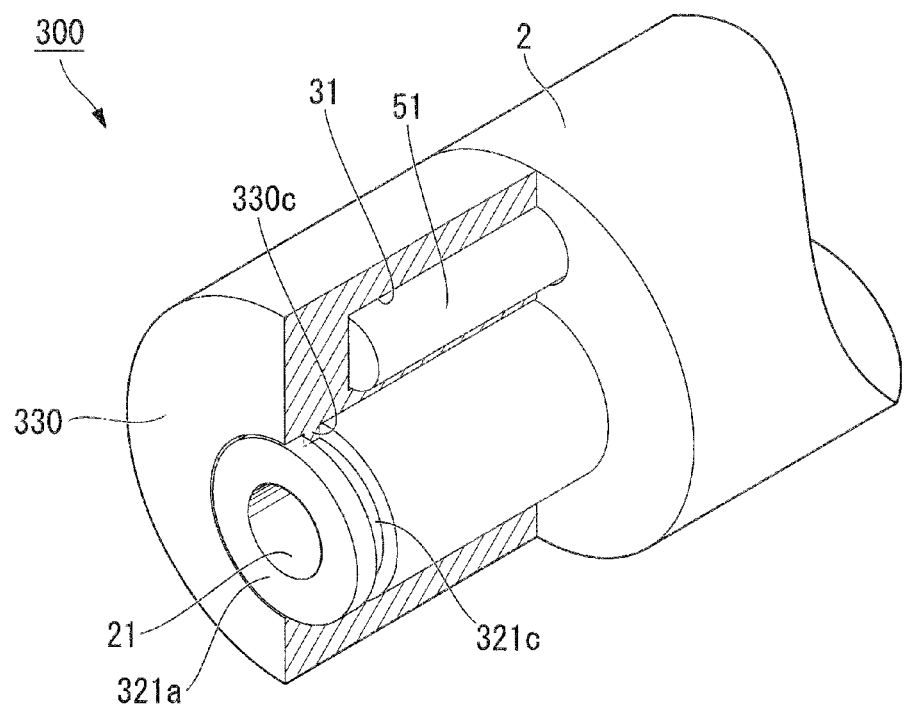
FIG. 11 is a perspective diagram of another example of a configuration of the treatment tool for endoscope in modification 3, showing a partial cross-section thereof.

FIG. 10 is a perspective diagram showing an enlargement of the distal-end side of the treatment tool for endoscope 300 of this modification, showing a partial cross-section thereof. The treatment tool for endoscope 300 of this modification includes an extended part 321*a* instead of the extended part 21*a*, and includes a passive electrode 330 instead of the passive electrode 30. In this modification, the angles of the outer faces of the passive electrode 330 can be formed smoothly, as with the passive electrode 30. The extended part 321*a* includes, on one part of its outer peripheral face, a fitting part 321*b*. The passive electrode 330 includes a fitted part 330*b* which the fitting part 321*b* fits into.

The fitting part 321*b* of the extended part 321*a* is a linear projection that protrudes radially outward from the outer peripheral face of the extended part 321*a* and extends in the circumferential direction of the extended part 321*a*, and the fitted part 330*b* of the passive electrode 330 is a linear groove that extends in the circumferential direction inside the passive electrode 330 such that the fitting part 321*b* can fit into it.

In this modification, when the extended part 321*a* and the passive electrode 330 are connected together, the elastic deformation of the extended part 321*a* enables the fitting part 321*b* to be inserted into the fitted part 330*b*. After the fitting part 321*b* and the fitted part 330*b* have been fitted together, the relative movement of the extended part 321*a* and the passive electrode 330 in the axial direction of the extended part 321*a* is restricted. Thus, according to the treatment tool for endoscope 300 of this modification, when the passive electrode 330 is connected to the extended part 321*a*, the passive electrode 330 can be prevented from falling out of the extended part 321*a*.

In this modification, the relationship between the linear projection and the linear groove can be reversed. That is, as shown in FIG. 11, the configuration can be one where a fitting part 321*c* of the extended part 321*a* is a linear groove that depresses radially inwards from the outer peripheral face of the extended part 321a and extends in the circumferential direction of the extended part 321a, and a fitted part 330c of the passive electrode 330 is a linear projection that fits into the fitting part 321c.

The linear projection need not be continuous in the circumferential direction. The linear groove need not be continuous in the circumferential direction, provided that it can be fitted to the linear projection.

[Modification 4]

Yet another modification of the treatment tool for endoscope of this embodiment will be explained with reference to FIGS. 12 to 17.

The configuration of a treatment tool for endoscope 400 of this modification differs from that in modification 3 described above in regard to the shapes of the fitting part and the fitted part.

Figure 12:
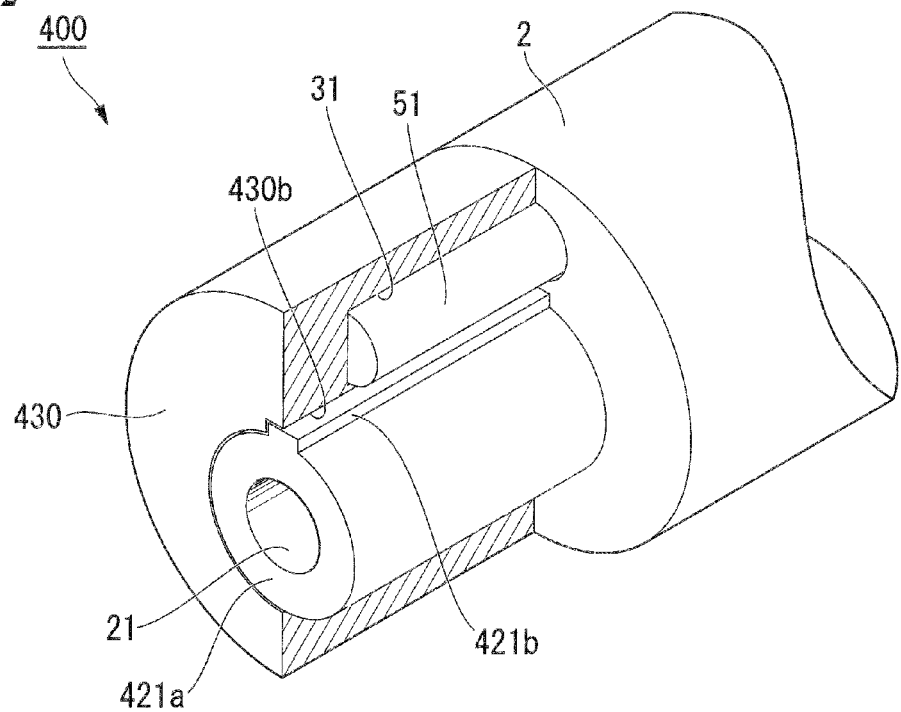
FIG. 12 is a perspective diagram showing an enlargement of one part of a treatment tool for endoscope in modification 4 of the embodiment of the invention, showing a partial cross-section thereof.

FIG. 12 is a perspective diagram showing an enlargement of the distal-end side of the treatment tool for endoscope 400 of this modification, showing a partial cross-section thereof. The treatment tool for endoscope 400 of this modification includes an extended part 421a instead of the extended part 21a, and includes a passive electrode 430 instead of the passive electrode 30. The extended part 421a includes, on one part of its outer peripheral face, a fitting part 421b. The passive electrode 430 includes a fitted part 430b which the fitting part 421b fits into.

The fitting part 421b of the extended part 421a is a linear projection that protrudes radially outward from the outer peripheral face of the extended part 421a and extends in the axial direction of the extended part 421a, and the fitted part 430b of the passive electrode 430 is a linear groove that extends in the axial direction on one part of the inner peripheral face of the passive electrode 430 such that the fitting part 421b can fit into it.

In this modification, when connecting the extended part 421a to the passive electrode 430, the linear projection-shaped fitting part 421b provided on the extended part 421a is aligned with and inserted into the linear groove-shaped fitting part 430b provided in the passive electrode 430. Therefore, the passive electrode 430 is prevented from rotating around the central axis of the first hole 21.

In the treatment tool for endoscope 400 of this modification, since the relative rotational movement of the passive electrode 430 and the extended part 421a about the axis is limited, it becomes easier to align the hole 31 in the passive electrode 430 with the second hole 22 in the sheath 2 (see FIG. 1), and easier to insert the electric cable 51 into the hole 31. It can therefore be made more convenient to assemble.

Figure 13:
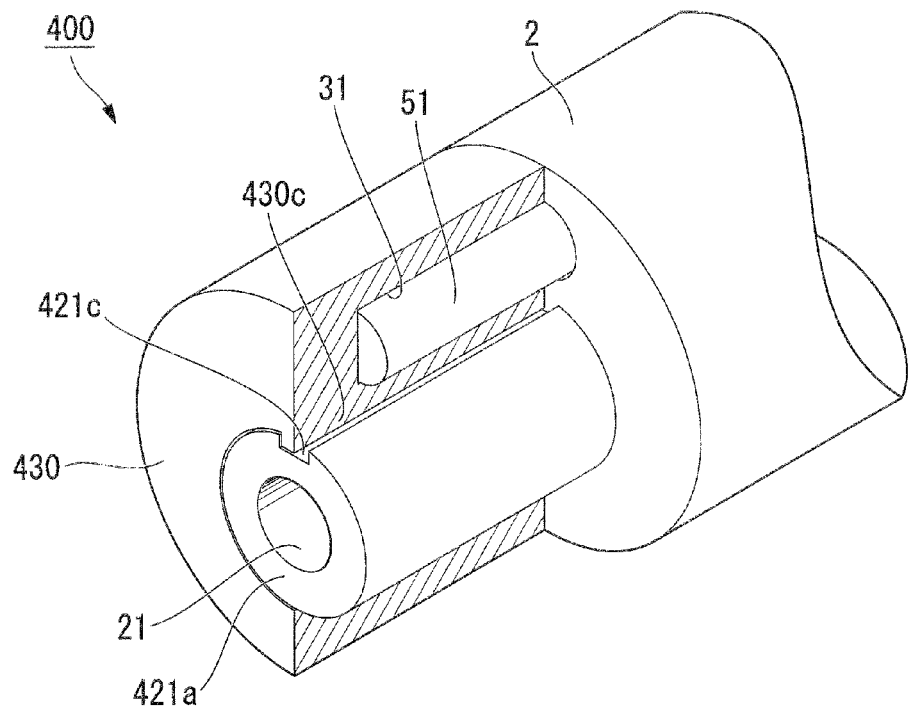
FIG. 13 is a perspective diagram of another first example of a configuration of the treatment tool for endoscope in modification 4, showing a partial cross-section thereof.

In this modification, as in modification 3 described above, the relationship between the linear projection and the linear groove can be reversed. That is, as shown in FIG. 13, the configuration can be one where a fitting part 421c of the extended part 421a is a linear groove that depresses radially inwards from the outer peripheral face of the extended part 421a and extends in the axial direction of the extended part, and a fitted part 430c of the passive electrode 430 is a linear projection that fits into the fitting part 421c.

Figure 14:
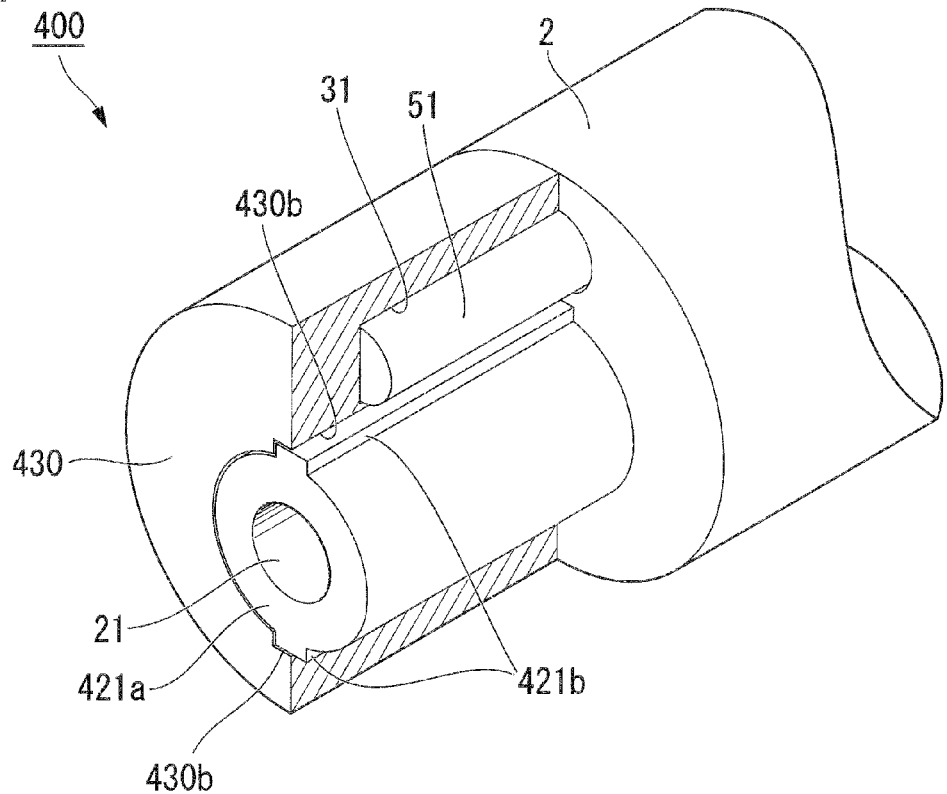
FIG. 14 is a perspective diagram of another second example of a configuration of the treatment tool for endoscope in modification 4, showing a partial cross-section thereof.

The fitting part 421b and the fitted part 430b are not limited to one pair. For example, as shown in FIG. 14, radially protruding fitting parts 421b can be formed in a plurality of portions that are circumferentially spaced about in the outer peripheral face of the extended part 421a, and fitted parts 430b for fitting to each of the fitting parts 421b can be formed in the passive electrode 430.

The shape of the extended part 421a for preventing the passive electrode 430 from rotating about the central axis of the first hole 21 is not limited to the shape which includes the fitting part 421b, and can be any shape wherein the contour of the radial cross-section of the extended part 421a is not circular. That is, the outer shape of the extended part 421a can be a non-cylindrical angular tube.

Figure 15:
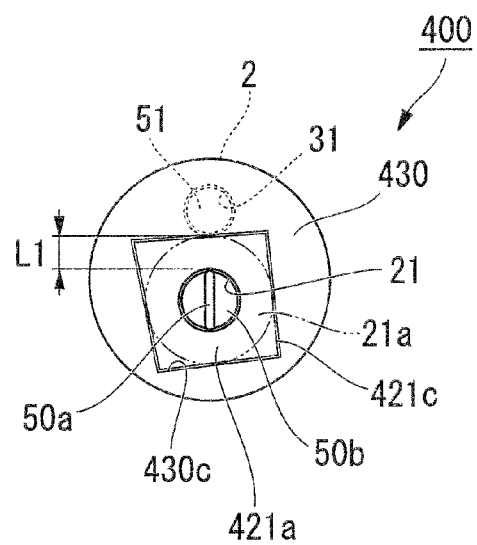
FIG. 15 is a front diagram of another third example of a configuration of the treatment tool for endoscope in modification 4.

FIG. 15 is a front diagram of the shape obtained by combining a fitting part and a fitted part shaped as the angular tube described above. The long dashed double-dotted line in FIG. 15 represents the contour of the cylindrical extended part 21a described above. As shown in FIG. 15, the configuration can be one where the extended part 421a includes a fitting part 421c formed such that the contour of its radial cross-section is quadrangular, and the passive electrode 430 includes a fitted part 430c formed such that, in radial cross-sectional view, it has a quadrangular shape that can be fitted to the fitting part 421c. When the contour of the radial cross-section of the extended part 421a is a multi-angled shape in this manner, the rotational positions of the extended part 421a and the passive electrode 430 in the circumferential direction can easily be aligned, since the fitting part 421c and the fitted part 430c are set at the point where they fit together.

Figure 16A:
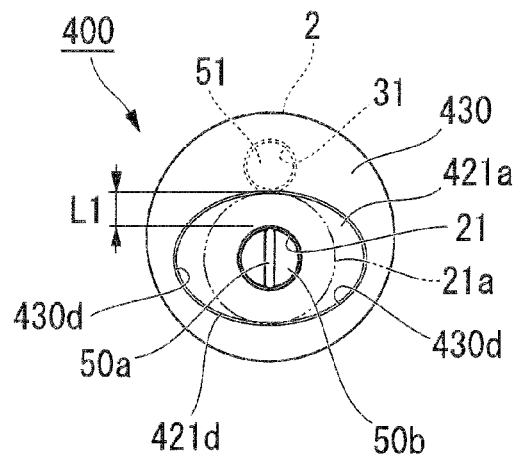
FIG. 16A is a front diagram of another fourth example of a configuration of the treatment tool for endoscope in modification 4.
Figure 16B:
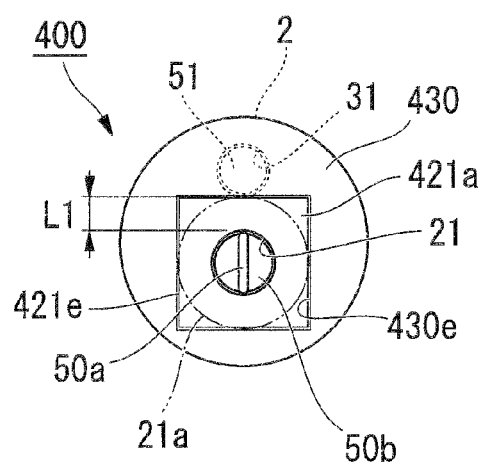
FIG. 16B is a front diagram of another fifth example of a configuration of the treatment tool for endoscope in modification 4.
Figure 16C:
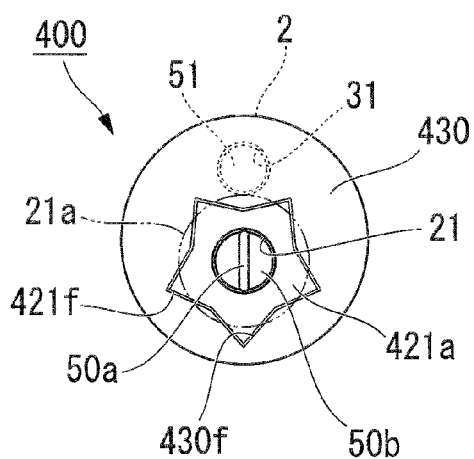
FIG. 16C is a front diagram of another sixth example of a configuration of the treatment tool for endoscope in modification 4.
Figure 17:
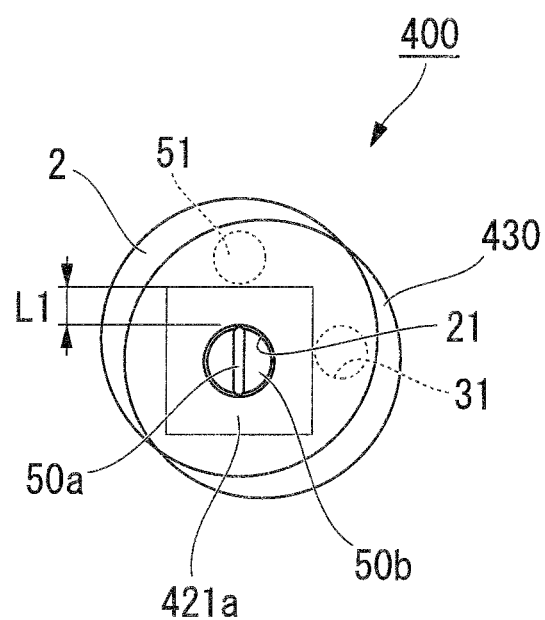
FIG. 17 is a front diagram showing a process of assembling the treatment tool for endoscope shown in FIG. 16B.

Other shapes for configuring the tubular extended part include the following. FIGS. 16A to 16C are front diagrams of other examples of the configuration of the extended part 421a.

As shown in FIG. 16A, the configuration can be one where the extended part 421a includes a fitting part 421d formed such that the contour of its radial cross-section is elliptical, and the passive electrode 430 includes a fitted part 430d formed such that, in radial cross-sectional view, it is formed in an elliptical shape that can be fitted to the fitting part 421d.

As shown in FIG. 16B, the configuration can be one where the extended part 421a includes a fitting part 421e formed such that the contour of its radial cross-section is square, and the passive electrode 430 includes a fitted part 430e formed such that, in radial cross-sectional view, it is formed as a square.

Moreover, as shown in FIG. 16C, the configuration can be one where the extended part 421a includes a fitting part 421f formed such that the contour of its radial cross-section is a star-shaped regular polygon, and the passive electrode 430 includes a fitted part 430f formed such that, in radial cross-sectional view, it is shaped as a star-shaped regular polygon that can be fitted to the fitting part 421f.

When the contour of the radial cross-section of the extended part 421a is a shape that has rotational symmetry, such as an ellipse or a regular polygon, as shown in FIGS. 16A to 16C, there are cases where the passive electrode 430 is attached in a plurality of orientations with respect to the extended part 421a. As for example shown in FIG. 17, there are cases where the extended part 421a and the passive electrode 430 are attached in an inappropriate orientation that differs from the one shown in FIG. 16B. However, when the central axis of the extended part 421a is eccentric to the central axis of the sheath 2, a step is formed between the outer peripheral face of the passive electrode 430 and the outer peripheral face of the sheath 2, making it easy to discover that the attachment position is incorrect.

[Modification 5]

Yet another modification of the treatment tool for endoscope of this embodiment will be explained with reference to FIGS. 18A and 18B.

In this modification, the configurations of the sheath, the passive electrode, and the electric cable differ from that of the treatment tool for endoscope described above.

Figure 18A:
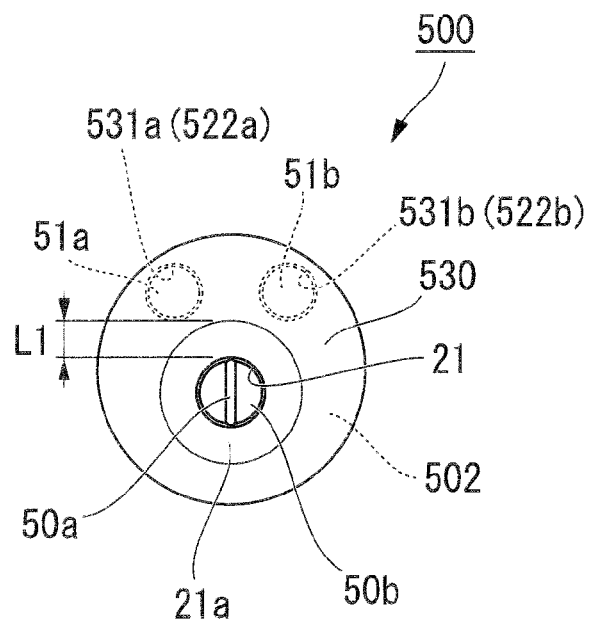
FIG. 18A is a front diagram showing an enlargement of one part of a treatment tool for endoscope in modification 5 in the embodiment of the invention.

FIG. 18A is a diagram of a treatment tool for endoscope 500 in this modification, viewed from the distal-end side.

Figure 18B:
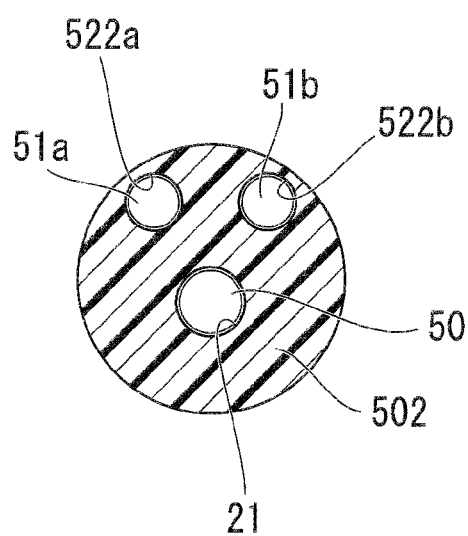
FIG. 18B is a radial cross-sectional diagram of a sheath in the treatment tool for endoscope in modification 5.

FIG. 18B is a radial cross-sectional diagram of the sheath in this modification. As shown in FIGS. 18A and 18B, the treatment tool for endoscope 500 includes a sheath 502 instead of the sheath 2, a passive electrode 530 instead of the passive electrode 30, and electric cables 51a and 51b instead of the electric cable 51. The sheath 502 includes a plurality of second holes 522a and 522b instead of the second hole 22. Instead of the electric cable 51, the electric cables 51a and 51b are inserted into the second holes 522a and 522b. Power can be supplied from the connector 66 of the operation part 4 to each of the electric cables 51a and 51b in similar manner to that described above.

Instead of the hole 31, holes 531a and 531b for inserting the electric cables 51a and 51b respectively are formed in the passive electrode 530.

Thus, in this modification, a plurality of electric cables are connected to the passive electrode 530 and conduct electricity to it. Therefore, the path of the electric cables connected to the passive electrode has more flexibility than in the case described above, in which the electric cable 51 is electrically connected to the passive electrode 30. Also, since the cross-sectional area of the electric cables can be made wider, impedance can be kept low when conducting a high-frequency current.

While a preferred embodiment of the present invention has been described above with reference to the drawings, the specific configuration is not limited to this embodiment. Design modifications and such like can be made without departing from the scope and spirit of the invention.

For example, while in this embodiment, the hole 31 is provided in the passive electrode 30 to connect the passive electrode 30 and the electric cable 51, the configuration is not limited to this. Instead of providing a hole for inserting the electric cable in the passive electrode, the electric cable can be fixed to an outer face of the passive electrode by welding or the like.

The constituent elements in the embodiment and the modifications described above can be combined as appropriate.

According to the invention, an object can be interposed between the high-frequency treatment part and the passive electrode, and a high-frequency current can be conducted to this object. At this time, since the sheath includes the first hole and the second hole, and has insulating properties, insulation is maintained between the wire inserted in the first hole and the electric cable inserted in the second hole. Moreover, since the extended part is formed at the distal end of the sheath, the passive electrode surrounding the outer periphery of the extended part is restricted from contacting the high-frequency treatment part which advances and retreats in the tubular extended part. Therefore, shorting of the high-frequency current is suppressed.

When the outer diameter of the extended part is smaller than the outer diameter of the sheath, the outer diameter of the passive electrode can be limited so that it is equal to or smaller than the outer diameter of the sheath. As a result, even when the passive electrode is disposed at the distal end of the sheath, slide resistance between the outer faces of the passive electrode and a channel, such as a forceps channel of the endoscope, is favorably reduced.

Since the positional relationship between the passive electrode disposed on the outer face of the extended part and the high-frequency snare inserted in the first hole is such that they are spaced apart by a predetermined thickness, contact between them is suppressed. Therefore, shorting of the high-frequency current conducted to the electric cable and the high-frequency snare is favorably suppressed, and the high-frequency current can be efficiently conducted to the object to be treated by the high-frequency snare.

According to the invention, since the passive electrode is disposed at the outer periphery of the extended part which protrudes from the distal end of the sheath further to the distal-end side, a simple configuration can achieve sufficient insulation between the passive electrode and the high-frequency treatment part.

What is claimed is:

1. A treatment tool for an endoscope, the treatment tool comprising:
   a passive electrode comprising a conductive body having:
      a distal external surface,
      a proximal external surface,
      a first internal surface extending through the conductive body to connect the distal external surface and the proximal external surface, wherein the first internal surface defines a first through-hole, and
      a second internal surface extending from the proximal external surface into the conductive body, wherein the second internal surface defines a cavity having a single cavity opening on the proximal external surface;
   an insulating sheath comprising an insulating body having:
      a first internal surface defining a second through-hole in the insulating body, wherein a portion of the first internal surface of the insulating body is provided within the first through-hole to insulate the second through-hole from the first internal surface of the conductive body of the passive electrode, and
      a second internal surface defining a third through-hole in the insulating body, wherein the third through-hole communicates with the cavity of the conductive body of the passive electrode through the single cavity opening on the proximal external surface of the conductive body of the passive electrode;
   an electric cable arranged within the third through-hole of the insulating body of the passive electrode and the cavity of the conductive body of the passive electrode, wherein the electric cable is mechanically and electrically connected to the second internal surface of the conductive body of the passive electrode; and
   an electrically conductive treatment instrument arranged within the second through-hole of the insulating sheath, wherein a distal end of the electrically conductive treatment instrument is configured to be advanced through the conductive body of the passive electrode to protrude from the distal external surface of the conductive body of the passive electrode to perform a treatment.

2. The treatment tool according to claim 1, wherein:
   the second through-hole has a circular cross-section, and
   the third through-hole has a circular cross-section.

3. The treatment tool according to claim 1, wherein outer-diameter dimensions of the passive electrode measured in a radial direction of the insulating sheath are smaller than outer-diameter dimensions of the insulating sheath in the radial direction of the insulating sheath.

4. The treatment tool according to claim 1, wherein a central axis of the second through-hole defined by the first internal surface of the insulating body is eccentric to a central axis of the insulating sheath.

5. The treatment tool according to claim 1,
   wherein the insulating body has an outer surface comprising:
      a first outer surface portion arranged radially from the portion of the first internal surface of the insulating body provided within the first through-hole, and a second outer surface portion arranged proximally of the first outer surface portion, and wherein an outer diameter of the first outer surface portion is smaller than a maximum outer diameter of the second outer surface portion.

6. The treatment tool according to claim 1, wherein the electrically conductive treatment instrument comprises an electrically conductive snare loop configured to be advanced through the second through-hole of the insulating sheath to protrude from the distal external surface of the conductive body of the passive electrode, to constrict a biological tissue within the electrically conductive snare loop, and to be retracted through the second through-hole to place the biological tissue in contact with the passive electrode such that the biological tissue provides a path for current flow between the passive electrode and the electrically conductive snare loop.

7. The treatment tool according to claim 1, wherein the electric cable is mechanically connected to the second internal surface of the conductive body of the passive electrode by one or more of:

welding the electric cable to the second internal surface of the conductive body of the passive electrode, press-fitting the electric cable against the second internal surface of the conductive body of the passive electrode, and crimping the passive electrode to compress the second internal surface of the passive electrode against the electric cable.

* * * * *